(12) United States Patent
Weigl et al.

(10) Patent No.: US 7,196,196 B2
(45) Date of Patent: Mar. 27, 2007

(54) SUBSTITUTED IMIDAZO[1,2-A]-5,6,7,8-TETRAHYDROPYRIDINE-8-ONES, METHOD FOR THEIR PRODUCTION AND THE USE THEREOF FOR PRODUCING IMIDAZO[1,2-A]PYRIDINES

(75) Inventors: Hagen Weigl, Ladenburg (DE); Klaus Ebel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 89 days.

(21) Appl. No.: 10/488,751

(22) PCT Filed: Sep. 3, 2002

(86) PCT No.: PCT/EP02/09813

§ 371 (c)(1),
(2), (4) Date: Mar. 9, 2004

(87) PCT Pub. No.: WO03/024963

PCT Pub. Date: Mar. 27, 2003

(65) Prior Publication Data

US 2005/0020620 A1    Jan. 27, 2005

(30) Foreign Application Priority Data

Sep. 14, 2001 (DE) .................. 101 45 457

(51) Int. Cl.
C07D 471/04 (2006.01)
C07D 471/14 (2006.01)

(52) U.S. Cl. ........................ 546/121; 546/82
(58) Field of Classification Search ......... 546/121, 546/82
See application file for complete search history.

(56) References Cited

U.S. PATENT DOCUMENTS

| 4,166,851 A | 9/1979 | Baldwin et al. |
| 5,112,834 A | 5/1992 | Senn-Bilfinger |
| 5,426,105 A | 6/1995 | Manning et al. |
| 5,574,042 A | 11/1996 | Oku et al. |
| 5,665,730 A | 9/1997 | Senn-Bilfinger et al. |
| 5,719,161 A | 2/1998 | Rainer |
| 5,980,585 A | 11/1999 | Terranova et al. |
| 6,096,758 A | 8/2000 | Grundler et al. |
| 6,124,313 A | 9/2000 | Grundler et al. |
| 6,132,768 A | 10/2000 | Sachs et al. |

FOREIGN PATENT DOCUMENTS

| CA | 2196075 | 2/1996 |
| DE | 28 20 938 | 11/1978 |
| DE | 196 02853 | 7/1997 |
| EP | 033 094 | 8/1981 |
| EP | 068 378 | 1/1983 |
| EP | 204 285 | 2/1986 |
| EP | 228 006 | 7/1987 |
| EP | 268 989 | 6/1988 |
| EP | 290 003 | 11/1988 |
| EP | 308 917 | 3/1989 |
| EP | 596 406 | 5/1994 |
| EP | 930 062 | 7/1999 |
| WO | 89/00570 | 1/1989 |
| WO | 94/18199 | 8/1994 |
| WO | 95/10518 | 4/1995 |
| WO | 96/03402 | 2/1996 |
| WO | 96/03405 | 2/1996 |
| WO | 98/37080 | 8/1998 |
| WO | 98/42707 | 10/1998 |
| WO | 98/54188 | 12/1998 |
| WO | 01/72748 | 10/2001 |
| WO | 01/72754 | 10/2001 |
| WO | 02/34749 | 5/2002 |

OTHER PUBLICATIONS

Kaminski et al. (1987) Journal Med. Chem. 30:2031-2046 is found in the specification on p. 1.
Derwent -97-386490/36.
Abe Y et al., (1998) J.Med.Chem. 41:564-578 is found in the specification on p. 1.
Derwent 88-316284/45—EP 290-003.
Pan et al., (1998) Tetrahedron Letters 39:8191-8194.
Tagat et al., (1995) Bioorg. Med. Chem. Lett. 5(18):2143-2146.
Kaiser et al., "Synthesis and Antimuscarinic Properties of Some N-Substituted 5-(aminomethyl)-3,3-Dipenyl-2(3H)-Furanone S"Journal of Medicinal Chem, American Chemical Society, Washington, U.S. vol. 35 No. 23, 1992, pp. 4415-4424.
Hafenbradl et al., (1996) Angew. Chem. Int. Ed. Engl. 33(5):545-547.
Schecchenko et al., (1992) Khim Geterotskikl Soedin 11, 1491-1493 (XP-002222931).
Bond et al, J. Chem. Soc. Perkin Trans. I vol. 19, 1993, 2241-2242 (XP-002222932).
Fukuda et al., Chem. Pharm. Bull, vol. 28, No. 6, 1980, 1667-172 (XP002222933).

Primary Examiner—Bernard Dentz
(74) Attorney, Agent, or Firm—Novak Druce & Quigg LLP

(57) ABSTRACT

A process for the preparation of imidazo[1,2-a]-5,6,7,8-tetra hydropyridin-8-ones by reaction of γ-butyrolactones with imidazols, novel imidazo[1,2-a]-5,6,7,8-tetrahydropyridin-8-ones, and their use for the preparation of imidazo[1,2-a] pyridines are described.

10 Claims, No Drawings

SUBSTITUTED IMIDAZO[1,2-A]-5,6,7,8-TETRAHYDROPYRIDINE-8-ONES, METHOD FOR THEIR PRODUCTION AND THE USE THEREOF FOR PRODUCING IMIDAZO[1,2-A]PYRIDINES

This application is the national stage of PCT/EP02/09813 filed Sep. 3, 2002.

The invention relates to substituted imidazo[1,2-a]-5,6,7,8-tetrahydropyridin-8-ones, processes for their preparation, and their use for the preparation of imidazo[1,2-a]pyridines.

Imidazo[1,2-a]pyridines are an economically extremely interesting class of compounds in the field of medicaments, crop protection agents and cosmetics.

Imidazo[1,2-a]pyridines are used especially for the prevention and treatment of various disorders, such as, for example, gastrointestinal disorders, cancer or disorders of the central nervous system. The preparation and use of compounds of this type is described, for example, for the treatment of gastrointestinal disorders such as gastric ulcers (Kaminski J J et al. (1987) J Med Chem 30:2031–2046; DE 28 20 938, WO 98/54188, WO 98/37080, DE 19602853, EP 0 308 917, EP 0 268 989, U.S. Pat. No. 6,124,313, US 6,096,758, US 6,132,768, WO 96/03405, WO 96/03402, U.S. Pat. No. 5,574,042, WO 95/10518, EP 596 406, WO 94/18199, WO 89/00570, EP 0 290 003, EP 0 228 006, EP 0 204 285, EP 068 378, EP 033 094). A product which may be mentioned is, for example, Solimidine® (Zolimidine® also Zolimidine®; 2[4-methylsulfonyl)phenyl]imidazo[1,2-a]pyridine). A cardiotonic medicament which may be further mentioned is the cAMP phosphodiesterase inhibitor Loprinone®, (Olprinone®, 1,2-dihydro-5-imidazo [1,2-a]pyridin-6-yl-6-methyl-2-oxo-3-pyridine carbonitrile). Furthermore, imidazo[1,2-a]pyridines find their way into nonbenzodiazepine hypnotics such as Zolpidem (N,N,6-trimethyl-2-p-tolylimidazo[1,2a]pyridine-3-acetamide). A curare mimetic which may furthermore be mentioned is fazadinium bromide (Fazadon®; 1,1'-azobis[3-methyl-2-phenylimidazo 1,2-a]pyridinium dibromide). A known anxiolytic is moreover Alpidem® (Ananxyl®, 6-chloro-2-(4-chlorophenyl)-N,N-dipropylimidazo [1,2-a]pyridine-3-acetamide). For the treatment of osteoporoses, minodronic acid (YM-529) is being evaluated in clinical investigations (1-hydroxy-2-imidazo[1,2-a]pyridin-3-ylethylidene) bisphosphonic acid). Other imidazo[1,2a]pyridines are in clinical trial as promising bradykinin (BK) B2 receptor antagonists (8-[[3-(N-acylglycyl-N-methylamino)-2,6-dichlorobenzyl]oxy]3-halo-2-methylimidazo[1,2-a]pyridine; Abe Y et al. (1998) J Med Chem 41:564–578). Finally, imidazo[1,2a]pyridines also go into nucleoside analogs which are used as antiviral therapeutics or in cancer therapy (chemotherapy) (Pan S F et al. (1998) Tetrahedron Letters 39:81.91-8194). Further compounds of this structural type are described as interleukin-6 inhibitors (e.g. 2,3,7,8-tetrahydro-4-aryl-1H-cyclopenta[e]imidazo[1,2-a]pyridin-5(6H)-one; Tagat J et al. (1995) Bioorg. Med. Chem. Lett. 5(18):2143–2146).

In cosmetics, imidazo[1,2-a]pyridines are employed, for example, as coupling components in oxidative hair dyes (EP 0 930 062).

Imidazo[1,2-a]pyridines are furthermore interesting synthesis units in crop protection agents. Herbicides such as Sulfosulfuron® (Maverick®, 1-(2-ethylsulfonylimidazo[1,2-a]pyridin-3-ylsulfonyl)-3-(4,6-demethoxypyrimidin-2-yl)urea) or Imazosulfuron® (Takeoff®, 1-(2-chloroimidazo[1,2-a]pyridin-3-yl-sulfonyl) -3-(4,6-dimethoxypyrimidin-2-yl)urea) comprise this grouping.

The synthesis of these compounds starts, inter alia, from the corresponding pyridine derivatives, to which the imidaxol ring is fused using various reaction pathways (Kaminski J J et al. (1987) J Med Chem 30:2031–2046; see also the abovementioned patents). The reaction as a rule comprise a number of reaction steps and require the availability of usually expensive starting materials.

WO 98/42707 outlines, in the context of a hypothetical synthesis process (p.16/scheme 8) the preparation of drugs starting from imidazo[1,2a]tetrahydropyridin-8-ones. However, no technical teaching at all is contained in the application, as these compounds are industrially accessible.

In the literature, as an imidazo[1,2a]tetrahydropyridin-8-one, only the natural substance Sibyllimycin (3-Methylimidazo[1,2a]tetrahydropyridin-8-one) and a process for its preparation are described (Hafenbradl et al. (1996) Angew. Chem. Int. Ed. Engl. 33(5):545–547). This synthesis is laborious, proceeds via a number of stages and is based on the N-alkylation of 4-methylimidazole with 4-bromobutyronitrile, cyclization using butyllithium and finally hydrolysis of the resulting imine.

The thermal reaction of γ-butyrolactones with 4,5-unsubstituted imidazoles is described and leads there to N-alkylated or N-acylated imidazoles without a ring closure being observed. Elevated temperatures (220° C.) lead to the addition of more butyrolactone molecules and—with longer reaction times—to tar formation (Shecchenko OK et al. (1992) Khim Geterotskikl Soedin 11, 1491–1493).

It is an object of the present invention to make available novel starting materials and processes for the preparation of imidazo[1,2a]pyridines.

Surprisingly, we have found that this object is achieved by preparation of imidazo[1,2a]-5,6,7,8-tetrahydropyridin-8-ones and a novel process for the preparation thereof.

A first subject of the invention relates to processes for the preparation of imidazo[1,2a]-5,6,7,8-tetrahydropyridin-8-ones, which comprises a) reacting a γ-butyrolactone with an imidazole which has at least one substitution in position 4 or 5, and b) isolating the imidazo[1,2a]-5,6,7,8-tetrahydropyridin-8-one.

The reaction can be carried out thermally at temperatures over 100° C., preferably at temperatures from 100 to 300° C., particularly preferably at temperatures from 150 to 250° C., very particularly preferably at temperatures from 190 to 220° C.

The reaction can be carried out without any additional activation or else alternatively by activation by addition of bases, acids or catalysts. Preferably, the activation is carried out by means of base catalysis. Preferred bases are potassium carbonates, cesium carbonates, sodiumhydroxide, potassiumhydroxide, DBU (1,5-diazabicyclo[5.4.0]undec-5-ylene, trialkylamines, LDA (lithiumdiisopropylamide) and Hünig's base (diisopropylethylamine).

The reaction of the imidazoles can be carried out using equimolar amounts of butyrolactone or an excess of one of the two starting materials—imidazole or γ-butyrolactone. In this case, the excess can be at least 20 mol %, preferably at least 50 mol %, particularly preferably at least 100 mol %, very particularly preferably at least 500 mol %. The preferred range of the excess is between 300 mol % and 500 mol %. Preferably, the reaction is carried out using an excess of γ-butyrolactone, which simultaneously serves as a solvent and for the trapping of the water of reaction.

In an advantageous embodiment, the excess γ-butyrolactone can possibly be partially or entirely distilled off together with resulting water of reaction during or after the reaction.

The isolated yield can be increased if, during or after the reaction, a part of the butyrolactone is distilled off.

In a further embodiment, another solvent, such as, for example, toluene or xylene, can be added to the reaction mixture which can favor, for example, in the function of an entraining agent, the removal of the water of reaction.

The reaction can be carried out at normal pressure, elevated pressure or reduced pressure. The pressure here can be kept constant during the reaction or else alternatively—for example for the purposes of distilling off a solvent—modulated. Preferably, the reaction is carried out at normal pressure.

The reaction time depends on the reaction rate. It can be, for example, approximately 12 hours. The imidazo[1,2a]-5,6,7,8-tetrahydropyridin-8-one can then be precipitated, for example, by cooling the batch and separated by solid/liquid separation ("filtering off with suction").

Methods which can be used for the purification of the crude product are the processes familiar to the person skilled in the art, such as column chromatography, high-pressure liquid chromatography or recrystallization, reprecipitation, zone-melting, distillation, washing with suitable solvents such as, for example, acetone, dibutyl ether, dibutyl ketone, isobutyl methyl ketone.

In a preferred embodiment, the invention relates to processes for the preparation of imidazo[1,2a]-5,6,7,8-tetrahydropyridin-8-ones of the formula Ia or Ib, which comprises a) reacting γ-butyrolactones of the formula III with imidazoles of the formula IIa or IIb, the imidazole having at least one substitution in position 4 or 5, and

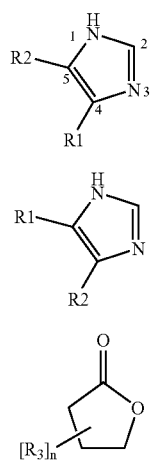

b) isolating imidazo[1,2a]-5,6,7,8-tetrahydropyridinones of the formula Ia or Ib.

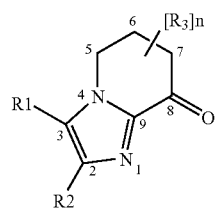

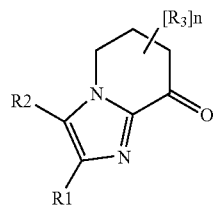

It is known to the person skilled in the art that imidazoles of the general formulae IIa and IIb can be converted into one another as a result of tautomerism.

Possible substituents on the imidazole and/or butyrolactone which are employed in the process according to the invention are preferably those which withstand the conditions of the process according to the invention without leading to an increased proportion of by-products or decomposition product. Preferably, starting materials are used which under the reaction conditions decompose by at most 50%, preferably to at most 20%, particularly preferably to at most 10%.

In a particular embodiment, the starting materials or individual substituents thereof employed in the process according to the invention can be derivatized for the period of the reaction in the manner familiar to the person skilled in the art or modified by known protective groups in order to increase the stability of the compounds under the conditions of the process according to the invention. Preferred derivatization or modification methods are oxidation, reduction, O-, S- or N-alkylation or acylation, such as esterification, etherification or acetal formation. Thus hydroxy groups can be protected, for example, by introduction of protective groups such as trityl, tert-butyldimethylsilyl, tert-butyloxycarbonyl (BOC), THP ethers or benzyl groups. Carbonyl groups can be protected by acetal formation, thiols as thioesters or thioethers; amines as carbamates, amides or benzylamines.

The invention further relates to substituted imidazo[1,2a]-5,6,7,8-tetrahydropyridin-8-ones described by the general formula Ia or Ib or salts thereof, with the proviso that a) R1, R2 and all radicals R3 are not simultaneously hydrogen, or
b) if R1 and all radicals R3 are hydrogen, then R2 is not methyl, or
c) if R2 and all radicals R3 are hydrogen, then R1 is not methyl, where the number of substituents R3 can assume a value n from 1 to 6.

For the process according to the invention and the substituted imidazo[1,2a]-5,6,7,8-tetrahydropyridin-8-ones according to the invention, the following preferably applies here in the abovementioned general formulae Ia, Ib, IIa, IIb or III:

R1, R2 or each R3 in each case and independently of one another is selected from the group consisting of hydrogen, halogen, hydroxyl, cyano, isocyano, thiocyano, amino, nitroso, nitro, carbonyl, alkylcarbonyl, sulfonate, alkylsulfonyl, sulfonamide, sulfonylurea, carboxyl, alkylcarboxyl, substituted or unsubstituted, branched or unbranched or cyclic alkyl, alkenyl, alkynyl, substituted or unsubstituted aryl or heteroaryl.

Preferably, R1, R2 or each R3 in each case and independently of one another is selected from the group consisting of hydrogen, hydroxyl, halogen, cyano, thiocyanato, branched or unbranched, optionally substituted $C_1$–$C_6$-alkyl, $C_2$–$C_6$-alkenyl, $C_2$–$C_6$-alkynyl, $C_3$–$C_7$-cycloalkyl, $C_3$–$C_6$-alkadienyl, hydroxy-$C_1$–$C_6$-alkyl, halo-$C_1$–$C_6$-alkyl, $C_1$–$C_6$-alkoxy, $C_2$–$C_6$-alkenyloxy, $C_1$–$C_6$-alkyloxy-$C_1$–$C_6$-alkyl, $C_1$–$C_6$-alkyloxy-$C_2$–$C_6$-alkenyl, $C_1$–$C_6$-alkyloxy-$C_2$–$C_6$-alkynyl, cyano-$C_1$–$C_6$-alkyl, isocyano-$C_1$–$C_6$-alkyl, amino-$C_1$–$C_6$-alkyl, amino-$C_2$–$C_6$-alkynyl, CO—$C_1$–$C_6$-alky, $C_1$–$C_6$-alkylsulfonyl, mono- or disubstituted N—($C_1$–$C_6$-alkyl)sulfonamide, sulfonylurea, sulfonate, carboxyl, $C_1$–$C_6$-alkylcarboxyl, carbonyl, formyl, alkylcarbonyl, aryl, arylalkyl, heteroaryl and heteroarylalkyl, preferred substituents being halogen, hydroxyl, cyano, isocyano, thiocyano, amino, nitroso, nitro, alkoxy, alkenyloxy, alkynyloxy, carbonyl or alkylcarbonyl, carboxyl or alkylcarboxyl. Preferably, R1 and R2 can also together form a ring system, such that a bicyclic imidazole is employed and a tricyclic imidazo[1,2a]-5,6,7,8-tetrahydropyridin-8-one is obtained.

If one of the starting materials employed contains a chiral center, one of the two enantiomers is preferably employed in the reaction.

The following very particularly applies to the selection of R1, R2 or each R3 in each case and independently of one another:

a) the halogen is fluorine.
b) $C_1$–$C_6$-alkyl is selected from the group consisting of methyl, ethyl, n-propyl, isopropyl, n-butyl, isobutyl, sec-butyl, tert-butyl, 1-methylpropyl, 2-methyl-propyl, n-pentyl, isopentyl, n-hexyl and isohexyl. Methyl, ethyl, n-propyl and isopropyl are most preferred.
c) $C_2$–$C_6$-alkenyl is selected from the group consisting of ethenyl, 1-propenyl, 2-propenyl, n-1-(or 2 or 3)-butenyl, isobutenyl, n-1-(or 2 or 3 or 4)pentenyl, isopentenyl, n-1-(or 2 or 3 or 5)-hexenyl and isohexenyl. Ethenyl, 1-propenyl and 2-propenyl are most preferred.
d) $C_3$–$C_6$-alkadienyl is selected from the group consisting of 1,2-propadienyl, n-butadien-1,3-yl, n-butadien-1,2-yl, n-butadien-2,3-yl, isobutadienyl, n-pentadienyl, isopentadienyl, n-hexadienyl and isohexadienyl. 1,2-Propadienyl and n-butadien-1,3-yl are most preferred.
e) $C_2$–$C_6$-alkynyl is selected from the group consisting of ethynyl, 1-propynyl, 2-propynyl, n-butyn-1-yl, n-butyn-2-yl, n-butyn-3-yl, 1-methylpropyn-2-yl, n-pentyn-1-yl, isopentynyl, n-hexynyl, isohexynyl. Ethynyl, 1-propynyl and 2-propynyl are most preferred.
f) $C_3$–$C_7$-cycloalkyl is selected from the group consisting of cyclopropyl, cyclobutyl, cyclopentyl, cyclohexyl and cyclohexyl. Preferably, R1 and R2 can also together form a ring system such that a bicyclic imidazole is employed and a tricyclic imidazo[1,2a]-5,6,7,8-tetrahydropyridin-8-one is obtained. R1 and R2 here preferably form a cyclopropyl, cyclobutyl, cyclopentyl, cyclohexyl or cyclohexyl ring system.
g) halo-$C_1$–$C_6$-alkyl is selected from the group consisting of halomethyl, haloethyl, n-halopropyl, isohalopropyl, n-halobutyl, tert-halobutyl, halo-1-methyl-propyl, halo-2-methylpropyl, n-halopentyl, isohalopentyl, n-halohexyl and isohalohexyl. Halomethyl, haloethyl, n-halopropyl and isohalopropyl are most preferred. One or more halogen substitutions are allowed here. The halogen is preferably fluorine. Trifluoromethyl is most preferred.
h) hydroxy-$C_1$–$C_6$-alkyl is selected from the group consisting of hydroxymethyl, hydroxyethyl, n-hydroxypropyl, isohydroxypropyl, n-hydroxybutyl, tert-hydroxybutyl, hydroxy-1-methylpropyl, hydroxy-2-methylpropyl, n-hydroxypentyl, isohydroxypentyl, n-hydroxyhexyl and isohydroxyhexyl. Hydroxymethyl, hydroxyethyl, n-hydroxypropyl and isohydroxypropyl are most preferred.
i) $C_1$–$C_6$-alkoxy is selected from the group consisting of methoxy, ethoxy, n-propoxy, 1-propoxy, n-butoxy, sec-butoxy, tert-butoxy, amyloxy, isoamyloxy and tert-amyloxy. Methoxy, ethoxy, n-propoxy and i-propoxy are most preferred.
j) $C_2$–$C_6$-alkenyloxy is selected from the group consisting of ethenoxy, n-propenyloxy, isopropenyloxy, n-butenyloxy and sec-butenyloxy.
k) $C_2$–$C_6$-alkynyloxy is selected from the group consisting of ethynyloxy, n-propynyloxy, isopropynyloxy, n-butynyloxy and sec-butynyloxy.
l) $C_1$–$C_6$-alkyloxy-$C_1$–$C_6$-alkyl is selected from the group consisting of methoxymethyl, ethoxymethyl, propoxymethyl, methyloxyethyl, ethoxyethyl, propoxyethyl, methoxypropyl, ethoxypropyl and propoxypropyl.
m) $C_1$–$C_6$-alkyloxy-$C_2$–$C_6$-alkenyl is selected from the group consisting of methyloxyethenyl, ethoxyethenyl, propoxyethenyl, methoxypropenyl, ethoxypropenyl and propoxypropenyl.
n) $C_1$–$C_6$-alkyloxy-$C_2$–$C_6$-alkynyl is selected from the group consisting of methyloxyethynyl, ethoxyethynyl, propoxyethynyl, methoxypropynyl, ethoxypropynyl and propoxypropynyl.
o) $C_2$–$C_6$-alkenyloxy-$C_1$–$C_6$-alkyl is selected from the group consisting of ethenoxymethyl, propenoxymethyl, ethenoxyethyl, propenoxyethyl, ethenoxypropyl and propenoxypropyl.
p) $C_1$–$C_6$-alkyloxy–$C_2$–$C_6$-alkynyl is selected from the group consisting of ethynoxymethyl, propynoxymethyl, ethynoxyethyl, propynoxyethyl, ethynoxypropyl and propynoxypropyl.
q) cyano-$C_1$–$C_6$-alkyl is selected from the group consisting of cyanomethyl (acetonitrile), cyanoethyl, n-cyanopropyl, isocyanopropyl, n-cyanobutyl, tert-cyanobutyl, cyano-1methylpropyl, cyano-2-methylpropyl, n-cyanopentyl, isocyanopentyl, n-cyanohexyl and isocyanohexyl. Cyanomethyl (acetonitrile), cyanoethyl, n-cyanopropyl and isocyanopropyl are most preferred.
r) Isocyano-$C_1$–$C_6$-alkyl is selected from the group consisting of isocyanomethyl, isocyanoethyl, n-isocyanopropyl, isoisocyanopropyl, n-isocyanobutyl, tert-isocyanobutyl, isocyano-1-methylpropyl, isocyano-2-methylpropyl, n-isocyanopentyl, isoisocyanopentyl, n-isocyanohexyl, isoisocyanohexyl. Isocyanomethyl, isocyanoethyl, n-isocyanopropyl and isoisocyanopropyl are most preferred.
s) Amino-$C_1$–$C_6$-alkyl is selected from the group consisting of aminomethyl, aminoethyl, n-aminopropyl, isoaminopropyl, n-aminobutyl, tert-aminobutyl, amino-1methylpropyl, amino-2-methylpropyl, n-aminopentyl, isoaminopentyl, n-aminohexyl, isoaminohexyl. Aminomethyl, aminoethyl, n-aminopropyl and isoaminopropyl are most preferred.
t) Amino-$C_2$–$C_6$-alkynyl is selected from the group consisting of aminoethynyl, 1-amino-1-propynyl, 1-amino-2-propynyl, n-1-aminobutyn-1-yl, n-1-aminobutyn-2-yl, n-1-aminobutyn-3-yl, 1-amino-3-methylpropyn-1-yl, n-1-aminopentynyl, n-1-aminohexynyl. Aminoethynyl, 1-amino-1propynyl and 1-amino-2-propynyl are most preferred.
u) $C_1$–$C_6$-alkylcarboxyl is selected from the group consisting of methylcarboxyl, ethylcarboxyl and propylcarboxyl.
v) $C_3$–$C_6$-cycloalkyl is selected from the group consisting of cyclopropyl, cyclobutyl, cyclopentyl, cyclopentenyl cyclohexyl, cyclohexenyl, cyclohexadienyl, imidazole and piperidine.

w) C$_1$–C$_6$-Alkylsulfonyl is selected from the group consisting of methylsulfonyl, ethylsulfonyl, n-propylsulfonyl, isopropylsulfonyl, n-butylsulfonyl, isobutylsulfonyl, sec-butylsulfonyl, tert-butylsulfonyl, (1-methylpropyl)sulfonyl, 2-methylpropylsulfonyl, n-pentylsulfonyl, isopentylsulfonyl, n-hexylsulfonyl and isohexylsulfonyl. Methylsulfonyl, ethylsulfonyl, n-propylsulfonyl and isopropylsulfonyl are most preferred.

x) With respect to the mono- or disubstituted N—(C$_1$–C$_6$-alkyl)sulfonamide, the alkyl is selected from the group consisting of methyl, ethyl, n-propyl, isopropyl, n-butyl, isobutyl, sec-butyl, tert-butyl, 1-methylpropyl, 2-methylpropyl, n-pentyl, isopentyl, n-hexyl and isohexyl, particularly preferably from the group consisting of methyl, ethyl, n-propyl and isopropyl. Very particularly preferably, with respect to the disubstituted N,N—(C$_1$–C$_6$-alkyl)sulfonamides, both substituents are identical.

y) Sulfonylurea can be substituted or unsubstituted, preferably substituted. The substitution can include substituted or unsubstituted alkyls or aryls or heteroaryls, 1-Sulfonyl-3-(4,6-dimethoxypyrimidin-2-yl)urea is very particularly preferred.

z) Aryl is selected from the group consisting of substituted and unsubstituted benzyl, substituted and unsubstituted naphthyl, phenyl, tolyl, xylyl, 1-naphthyl, 2-naphthyl, 1-anthryl and 2-anthryl are very particularly preferred.

aa) Heteroaryl is selected from the group consisting of substituted and unsubstituted aromatic heterocycles, substituted and unsubstituted aromatic or partially aromatic heterobicycles, where the heterocycles are 5- or 6-membered rings and can contain up to 3 heteroatoms selected from the group consisting of N,O,S.

In a preferred embodiment, the process according to the invention is carried out starting from imidazoles which in each case carry a substitution which is different from hydrogen both in position 4 and position 5.

In a particularly preferred embodiment, the process according to the invention is carried out starting from imidazoles which in each case carry an identical substitution which is different from hydrogen both in position 4 and position 5.

This embodiment is particularly advantageous, since only one product results and thus the compounds of the general formulae Ia and Ib correspond. Since the yields of the desired product are particularly good here, this embodiment can be realized particularly advantageously economically.

The substituted imidazo[1,2a]-5,6,7,8-tetrahydropyridin-8-ones according to the invention preferably include those which carry a substitution other than hydrogen both in position 2 and position 3. Very particularly preferably, these substitutions which are other than hydrogen are identical in positions 2 and 3.

Very particularly preferred combinations of R1, R2 and R3 with respect to the imidazo[1,2-a]-5,6,7,8-tetrahydropyridin-8-ones to be prepared by the process according to the invention are mentioned below:

1. R3=H, R1=R2=methyl. γ-butyrolactone and 4,5-dimethylimidazole or derivatives or modifications of the abovementioned are employed. 2,3-Dimethylimidazo[1,2-a]-5,6,7,8-tetrahydropyridin-8-one results.

2. R3=H, R1=H, R2=methyl. γ-butyrolactone and 4-methylimidazole (or alternatively 5-methylimidazole) are employed.
2-Methylimidazo[1,2a]-5,6,7,8-tetrahydropyridin-8-one and 3-methylimidazo[1,2-a]-5,6,7,8-tetrahydropyridin-8-one result.

3. R3=H, R2=methyl, R1=acetonitrile (cyanomethyl).
γ-Butyrolactone and 4-acetonitrile-5-methylimidazole or 5-acetonitrile-4-methylimidazole or derivatives or modifications of the abovementioned are employed. The reaction affords 2-methyl-3-acetonitrileimidazo[1,2-a]-5,6,7,8-tetrahydropyridin-8-one and 3-methyl-2-acetonitrileimidazo[1,2-a]-5,6,7,8-tetrahydropyridin-8-one, 2-methyl-3-acetonitrileimidazo[1,2-a]-5,6,7,8-tetrahydropyridin-8-one being the preferred product.

4. R3 =methyl in position 6 of the imidazopyrimidine system or the β-position of the γ-butyrolactone, R2=4-methylphenyl, R1=N,N-dimethylacetamide. β-Methyl-γ-butyrolactone and 5-N,N-dimethylacetamide-4-(4-methylphenyl)imidazole or 4-N,N-dimethylacetamide-5-(4-methylphenyl)imidazole or derivatives or modifications of the abovementioned are employed. N,N,6-Trimethyl-2-(4-methylphenyl)-imidazo[1,2-a]-5,6,7,8-tetrahydropyridin-8-one-3-acetamide and N,N,6-trimethyl-3-(4-methylphenyl)imidazo[1,2-a]-5,6,7,8-tetrahydropyridin-8-one-2-acetamide result, N,N,6-trimethyl-2-(4-methylphenyl)imidazo[1,2-a]-5,6,7,8-tetrahydropyridin-8-one-3-acetamide being the preferred product.

5. R3=H, R2=chlorine, R1=sulfonyl-3-(4,6-dimethoxypyrimidin-2-yl)urea).
γ-butyrolactone and (4-chloroimidazole-5-yl -sulfonyl)-3-(4,6-dimethoxypyrimidin-2-yl)urea or (5-chloroimidazole-4-yl-sulfonyl)-3-(4,6-dimethoxypyrimidin-2-yl)urea or derivatives, precursors or modifications of the abovementioned are employed. Preferably, the sulfonylurea side chain is only synthesized after the reaction of imidazole and γ-butyrolactone. To this end, the starting material employed would be the corresponding compound where R1=sulfonyl.
1-(2-Chloroimidazo[1,2-a]-5,6,7,8-tetrahydropyridin-8-one-3-yl-sulfonyl)-3-(4,6-dimethoxypyrimidin-2-yl)urea and 1-(3-chloroimidazo[1,2-a]-5,6,7,8-tetrahydropyridin-8-one-2-yl-sulfonyl)-3-(4,6-dimethoxypyrimidin-2-yl,)urea, 1-(2-chloroimidazo[1,2-a]-5,6,7,8-tetrahydropyridin-8-one-3-yl-sulfonyl)-3-(4,6-dimethoxypyrimidin-2-yl)urea being the preferred product.

6. R3=H, R2=ethylsulfonyl, R1=sulfonyl-3-(4,6-dimethoxypyrimidin-2-yl)urea). γ-Butyrolactone and (4-ethylsulfonylimidazole-5-yl-sulfonyl)-3-(4,6-dimethoxypyrimidin-2-yl)urea or (5-ethylsulfonylimidazole-4-yl-sulfonyl)-3-(4,6-dimethoxypyrimidin-2-yl)urea or derivatives, precursors or modifications of the abovementioned are employed. Preferably, the sulfonylurea side chain is synthesized only after the reaction of imidazole and γ-butyrolactone. To this end, the starting material employed would be the corresponding compound where R1=sulfonyl. 1-(2-Ethylsulfonylimidazo[1,2-a]-5,6,7,8-tetrahydropyridin-8-on-3-yl-sulfonyl)-3-(4,6-dimethoxypyrimidin-2-yl)urea and 1-(3-ethylsulfonylimidazo[1,2-a]-5,6,7,8-tetrahydropyridin -8-one-2-yl-sulfonyl)-3-(4,6-dimethoxypyrimidin-2-yl)urea, result, 1-(2-ethylsulfonylimidazo[1,2-a]-5,6,7,8-tetrahydropyridin-8-on-3-yl-sulfonyl)-3-(4,6-dimethoxypyrimidin-2-yl)urea being the preferred product.

7. R3=H, R2=methyl, R1=amino. 4-Methyl -5-aminoimidazole or 5-methyl-4-aminoimidazole and γ-butyrolactone or derivatives or modifications of the abovementioned are employed. For example, the amino function can be present protected in the form of an amide. 3-Amino-2-methylimidazo[1,2-a]-5, 6,7,8-tetrahydropyridin-8-one and 2-amino-3-methylimidazo[1,2-a]-5,6,7,8-tetrahydropyridin-8-one result, 3-amino-2-methylimidazo[1,2-a]-5,6,7,8-tetrahydropyridin-8-one being the preferred product.

8. R3=H, R1=formyl, R2=methyl. 4-Methyl-5-formylimidazole or 5-methyl-4-formylimidazole and γ-butyrolactone or derivatives or modifications of the abovementioned are employed. The carbonyl function can be present, for example, protected in the form of an acetal. 3-Formyl-2-methylimidazo[1,2-a]-5,6,7,8-tetrahydropyridin-8-one and 2-formyl-3-methylimidazo[1,2-a]-5,6,7,8-tetrahydropyridin -8-one result, 3-formyl-2-methylimidazo[1,2-a]-5,6,7,8-tetrahydropyridin-8-one being the preferred product.

9. R3=H, R1=hydroxymethyl, R2=methyl.
4-Methyl-5-hydroxymethylimidazole or 5-methyl -4-hydroxymethylimidazole and γ-butyrolactone or derivatives or modifications of the abovementioned are employed. The hydroxyl function can be present, for example, protected in the form of an ester. 3-Hydroxymethyl-2-methylimidazo[1,2-a]-5,6,7,8-tetrahydropyridin-8-one and 2-hydroxymethyl-3-methylimidazo[1,2-a]-5,6,7,8-tetrahydropyridin-8-one result, 3-hydroxymethyl-2-methylimidazo[1,2-a]-5,6,7,8-tetrahydropyridin-8-one being the preferred product.

10. R3=methyl in-position 7 of the imidazopyrimidone system, R2 =methyl, R1=amino. 4-Amino-5-methylimidazole or 5-amino-4-methylimidazole and a-methyl-γ-butyrolactone or derivatives or modifications of the abovementioned are employed. The aminofunction can be present, for example, protected in the form of an amide. 3-Amino-2,7-dimethylimidazo[1,2-a]-5,6,7,8-tetrahydropyridin-8-one and 2-amino-3,7-dimethylimidazo[1,2-a]-5,6,7,8-tetra-hydropyridin-8-one results, 3-amino-2,7-dimethyl -imidazo[1,2-a]-5,6,7,8-tetrahydropyridin-8-one being the preferred product.

11. R3=H, R1=formyl (carbonyl), R2=H. 5-Formylimidazole or 4-formylimidazole and γ-butyrolactone and derivatives or modifications of the abovementioned are employed. The carbonyl function can be present, for example, protected in the form of an acetal. For example, imidazole-4-acetate(obtainable, for example, from SIGMA-ALDRICH) or esters of this compound can be employed which, after reaction —if appropriate after hydrolysis—are converted reductively to formyl. 3-Formylimidazo[1,2-a]-5,6,7,8-tetra -hydropyridin-8-one and 2-formylimidazo[1,2-a]-5,6,7,8-tetrahydropyridin-8-one result, 3-formylimidazo[1,2-a]-5,6,7,8-tetrahydropyridin-8-one being the preferred product.

12. R3=methyl in position 7 of the imidazopyrimidone system, R1=formyl (carbonyl), R2=H. 5-Formylimidazole or 4-formylimidazole and α-methyl-γ-butyrolactone or derivatives or modifications of the abovementioned are employed. The carbonyl function can be present, for example, protected in the form of an acetal. For example, imidazole-4-acetate (obtainable from SIGMA-ALDRICH) or esters of this compound can also be employed which, after reaction—if appropriate after hydrolysis—are converted reductively to formyl. 3-Formyl-7-methylimidazo[1,2-a]-5,6,7,8-tetrahydropyridin -8-one and 2-formyl-7-methylimidazo[1,2-a]-5,6,7,8-tetrahydropyridin-8-one result, 3-formyl-7-methylimidazo[1,2-a]-5,6,7,8-tetrahydropyridin-8-one being the preferred product.

13. R3=H, R1=R2=ethoxycarbonyl.
4,5-Diethoxycarbonylimidazole and γ-butyrolactone or derivatives or modifications of the abovementioned are employed. 2,3-Diethoxycarbonylimidazo[1,2-a]-5,6,7,8-tetrahydropyridin -8-one results.

14. R3=H, R1=R2=(N,N-diethylamino)carbonyl.
4,5-(N,N-diethylamino)carbonylimidazole and γ-butyrolactone or derivatives or modifications of the abovementioned are employed. 2,3-(N,N-diethylamino)carbonylimidazo[1,2-a]-5,6,7,8-tetrahydropyridin-8-one results.

15. R3=dimethylamino in position 7 of the imidazopyrimidone system, R1=methyl, R2=H. 4-methylimidazole or 5-methylimidazole and α-dimethylamino-γ-butyrolactone or derivatives or modifications of the abovementioned are employed. 7-Dimethylamino-2-methyl-imidazo[1,2-a]-5,6,7,8-tetrahydropyridin-8-one and 7-dimethylamino-3-methylimidazo[1,2-a]-5,6,7,8-tetrahydropyridin-8-one result, 7-dimethylamino-2-methylimidazo[1,2-a]-5,6,7,8-tetrahydropyridin-8-one being the preferred product.

16. R3=methyl in position 7 of the imidazopyrimidone system, R1=R2=ethoxycarbonyl. 4,5-Diethoxyimidazole and α-methyl-γ-butyrolactone or derivatives or modifications of the abovementioned are employed. 2,3-Diethoxycarbonyl-7-methylimidazo[1,2-a]-5,6,7,8-tetrahydropyridin-8-one results.

17. R3=methyl in position 7 of the imidazopyrimidone system, R1=methyl, R2=H. 4-Methylimidazole or 5-methylimidazole and α-methyl-γ-butyrolactone or derivatives or modifications of the abovementioned result. 2,7-Dimethylimidazo[1,2-a]-5,6,7,8-tetrahydropyridin-8-one and 3,7-dimethylimidazo[1,2-a]-5,6,7,8-tetrahydropyridin-8-one result, 2,7-dimethylimidazo[1,2-a]-5,6,7,8-tetrahydrbpyridin-8-one being the preferred product.

Derivatives and modifications means with respect to the abovementioned starting materials for the preparation of the preferred imidazo[1,2-a]-5,6,7,8-tetrahydropyridin-8-ones, for example, those chemical modifications which provide an increased stability of the starting materials under the reaction conditions of the process according to the invention. Thus the carbonyl or formyl group, for example, can be protected in the form of an acetal.

4,5-Substituted imidazoles are accessible in various ways known to the person skilled in the art. Syntheses are described in Houben-Weyl, Methoden der organischen Chemie [Methods of organic chemistry], Volume E8c, Hetarene III—Part 3, 4th edition, Ed. E. Schaumann, Georg Thieme Verlag Stuttgart, 1994, Chapter 1, pp. 1–192. Further methods are described in M. Ross Grimmett (1997) imidazole and Benzimidazole Synthesis, Academic Press, Inc., San Diego, Calif,. USA. Various imidazoles can be obtained commercially (e.g. 4-methylimidazole, 4-phenylimidazole, imidazole-4,5-dicarboxylic acid, imidazole-4-acetate at SIGMA-ALDRICH/Fluka, Histamine, Histidine at Aldrich).

Substituted γ-butyrolactones are accessible, inter alia, from substituted 1,4-butanediols or substituted tetrahydrofurans in the manner familiar to the person skilled in the art. Customary synthesis processes are described, inter alia, in Houben-Weyl "Methoden der org. Chemie" Volume 6/2 Oxygen compounds I Part 2; Author H. Krbper; p. 571ff, 1963. Substituted γ-butyrolactones are accessible, for example, from tetrahydrofurans or substituted γ-halogenated butyric acid derivatives, such as 4-bromobutyric acid. Various syntheses are known to the person skilled in the art (JACS 51; 260 (1929); JACS 52; 3702–4 (1930); JACS 63; 2488 (1941); JACS 71; 2825–26 (1949); JACS 80; 6682-84; CA 53; 15050; CA 54; 4393i; CA 59; 11234e).

For example, the following γ-butyrolactones or γ-butyrolactones derived from these or derivatized by the synthesis steps familiar to the person skilled in the art can be employed which can be obtained commercially (for example via the firms SIGMA-ALDRICH or FLUKA):

γ-Butyrolactone
α-Methyl-γ-butyrolactone
γ-Methyl-γ-butyrolactone (γ-valerolactone)
α-Methylene-γ-butyrolactone (tulipane)
γ-Methylene-γ-butyrolactone (a'-angelicalactone)
γ-Ethyl-γ-butyrolactone (γ-caprolactone)
γ-Propyl-γ-butyrolactone
γ-Pentyl-γ-butyrolactone
γ-Hexyl-γ-butyrolactone
γ-Heptyl-γ-butyrolactone
γ-Octyl-γ-butyrolactone
γ-Phenyl-γ-butyrolactone
R(−)-γ-Ethoxycarbonyl-γ-butyrolactone
γ-Jasmolactone (cis-γ-(3-hexen-1-yl)butyrolactone)
γ-(2-Naphthyl)-γ-butyrolactone
α,α-Diphenyl-γ-butyrolactone
α-Acryloyloxy-β, β-dimethyl-γ-butyrolactone
α-Hydroxy-β,β-dimethyl-γ-butyrolactone
4-Hydroxy-2, 2-diphenyl-γ-butyrolactone
α-Amino-γ-butyrolactone
(S)-2-Amino-4-butyrolactone (L-homoserine lactone)
2-(Z-Amino)-4-butyrolactone
α-Hydroxy-γ-butyrolactone
β-Hydroxy-γ-butyrolactone
γ-Hydroxymethyl-γ-butyrolactone
γ-Trityloxymethyl-γ-butyrolactone
γ-Tosyloxymethyl-γ-butyrolactone
γ-Ethoxycarbonyl-γ-butyrolactone
γ-Carboxy-γ-butyrolactone
2-Acetylbutyrolactone
2-Bromo-γ-butyrolactone
α-Bromo-α-methyl-γ-butyrolactone
2-Bromo-4-hydroxy-γ-butyrolactone
Pantolactone (2-hydroxy-3,3-dimethyl-γ-butyrolactone)
α-Acetyl-α-methyl-γ-butyrolactone
γ-Phenyl-α-trifluoromethyl-γ-butyrolactone
α-Benzylidene-γ-butyrolactone If the γ-butyrolactone to be employed contains a chiral center, one of the two enantiomers is preferably employed.

A further subject of the invention relates to the use of the imidazo[1,2a]-5,6,7,8-tetrahydropyridin-8-ones according to the invention as in formula Ia or Ib for the preparation of imidazo[1,2a]pyridines, preferably as in the general formula IV, and of compounds of the general formula V and their precursors or intermediates.

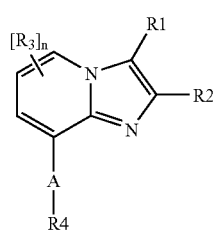

IV

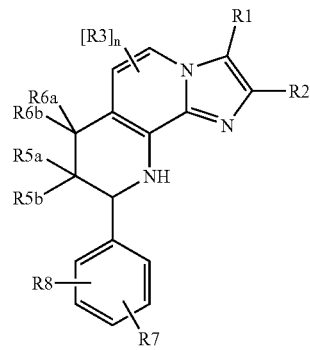

V

The following applies here for the general formula IV:

a) for the radicals R1, R2 or each R3 in each case and independently of one another the definitions given above, and
b) A is O or NH, and
c) R4 is substituted or unsubstituted, branched or unbranched $C_1$–$C_6$-alkyl, $C_2$–$C_6$-alkenyl, $C_2$–$C_6$-alkynyl, $C_3$–$C_7$-cycloalkyl, $C_3$–$C_6$-alkadienyl, halo-$C_1$–$C_6$-alkyl, $C_1$–$C_6$-alkoxy, $C_2$–$C_6$-alkenyloxy, $C_2$–$C_6$-alkynyloxy, $C_1$–$C_6$-alkyloxy-$C_1$–$C_6$-alkyl, $C_1$–$C_6$-alkyloxy-$C_2$–$C_6$-alkenyl, $C_1$–$C_6$-alkyloxy-$C_2$–$C_6$-alkynyl, cyano-$C_1$–$C_6$-alkyl, isocyano-$C_1$–$C_6$-alkyl, amino-$C_1$–$C_6$-alkyl, amino-$C_2$–$C_6$-alkynyl, CO-$C_1$–$C_6$-alkyl, carboxyl, $C_1$–$C_6$-alkylcarboxyl, substituted or unsubstituted aryl, arylalkyl, heteroaryl and heteroarylalkyl.

The following applies for the general formula V:

a) for the radicals R1, R2 or each R3 in each case and independently of one another the definitions given above, and
b) R5a and R5b are selected from the group consisting of hydrogen, hydroxyl, $C_1$–$C_6$-alkoxy, $C_1$–$C_6$-alkoxy-$C_1$–$C_6$-alkoxy, $C_1$–$C_6$-alkylcarbonyloxy. R5a and R5b can also together be oxygen (Oxo group), and
c) R6a and R6b are selected from the group consisting of hydrogen, hydroxyl, $C_1$–$C_6$-alkoxy, $C_1$–$C_6$-alkoxy-$C_1$–$C_6$-alkoxy, $C_1$–$C_6$-alkylcarbonyloxy, at least one of the radicals R6a or R6b being hydrogen. R6a and R6b can also together be oxygen (Oxo group), and
d) R7 is hydrogen, halogen, $C_1$–$C_6$-alkyl, $C_1$–$C_6$-alkoxy, $C_1$–$C_6$-alkoxycarbonylamino, $C_1$–$C_6$-alkoxy-$C_1$–$C_6$-alkoxycarbonylamino or trifluoromethyl, and
e) R8 is hydrogen, halogen, $C_1$–$C_6$-alkyl, $C_1$–$C_6$-alkoxy or salts thereof.

Particularly preferred compounds of the general-formula IV are mentioned in Kaminski J J et al. (1987) J Med Chem 30:2031–2046; DE 28 20 938, WO 98/54188, WO 98/37080, DE 19602853, EP 0 308 917, EP 0 268 989, U.S. Pat. No. 6,124,313, US 6,096,758, WO 96/03405, WO 96/03402, U.S. Pat. No. 5,574,042, WO 95/10518, EP 596 406, WO 94/18199, WO 89/00570, EP 0 290 003, EP 0 228 006, EP 0 204 285, EP 068 378, EP 033 094, U.S. Pat. No. 6,132,768.

Particularly preferred compounds of the general formula V are mentioned in WO 98/42707.

These compounds are accessible according to the reactions shown in schemes A to C using processes familiar to the person skilled in the art.

Thus it is possible, for example, starting from an imidazo[1,2-a]-5,6,7,8-tetrahydropyridin-8-one to carry out the formation of Schiff's bases by reaction with alkyl- or arylamines. Preferably, the amine is employed in excess and the reaction is carried out under acidic catalysis, for example with p-toluenesulfonic acid (as described, for example, in: Organikum, Deutscher Verlag der Wissenschaften (1990); Chapter 7.1.1). The Schiff's bases obtained (enamines) can then be converted by oxidative aromatization to substituted 8-aminoimidazo[1,2a]pyridines according to reaction scheme A(II). Alternatively, imidazo[1,2-a]-5,6,7,8-tetrahydropyridin-8-ones can be converted by reaction with ammonia and subsequent oxidative aromatization to imidazo[1,2a]pyridines and the preferred compounds can be obtained by reaction, for example, with haloalkyls or -aryls (scheme A(I)). 8-Hydroxyimidazo[1,2a]-pyridines are directly accessible by oxidative aromatization.

Oxidative aromatization can be realized, for example, by reaction with 2,3-dichloro-5,6-dicyanobenzoquinone (DDQ) in the manner familiar to the person skilled in the art (overview article: Walker D. et al. (1967) Chem. Rev. 67:153–195). A further atomization variant which can be used is bromination and subsequent HBr elimination.

The reactions of 8-hydroxyimidazo[1,2a]pyridines or 8-aminoimidazo[1,2a]pyridines according to reaction schemes A(I) or B are carried out using hydroxy- or haloalkyls or aryls—if appropriate after in situ derivatization or activation—is described, for example, in U.S. Pat. No. 6,124,313, EP 0 033 094, EP 0 308 917 or EP 0 268 989.

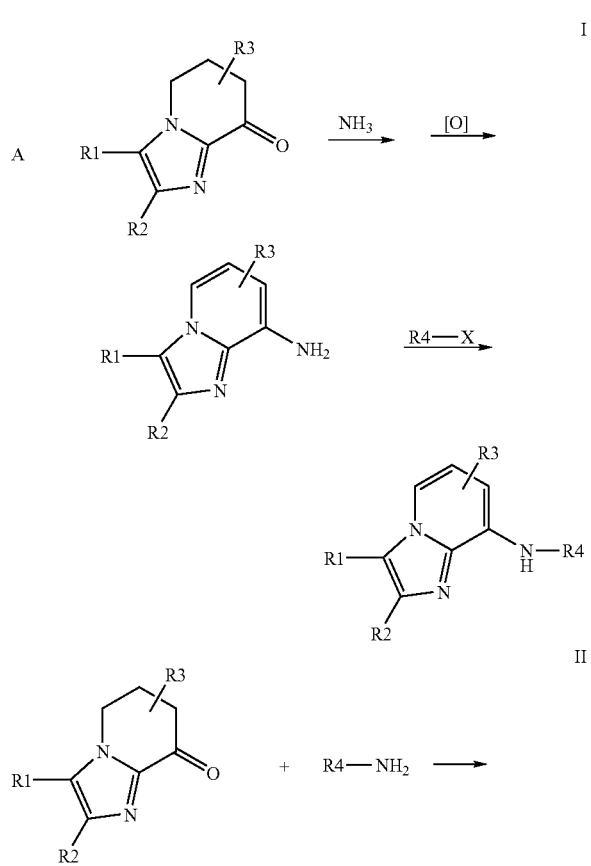

Thus 2,3-dimethylimidazo[1,2-a]-5,6,7,8-tetrahydropyridin-8-one, for example, can be converted by reaction with alkyl or arylhalides, preferably alkyl or arylbromides, and subsequent aromatization by oxidation to 2,3-dimethyl-8-alkyl/aryloxyimidazo[1,2-a]pyridines. Furthermore, a reaction of 2,3-dimethylimidazo[1,2-a]-5,6,7,8-tetrahydropyridin-8-one with alkyl- or arylamines and subsequent aromatization by oxidation to 2,3-dimethyl-8-alkyl/arylaminoimidazo[1,2-a]pyridines can be carried out.

2-Methyl-3-acetonitrileimidazo[1,2-a]pyridin-8-one can be converted by reaction with bromomethylbenzene and subsequent aromatization by oxidation to 2-methyl-8-(phenylmethoxy)imidazo[1,2-a]pyridine-3-acetonitrile, a promising compound for the treatment of gastric ulcers. The compound is known under the name SCH-28080 and functions as an inhibitor of gastric H+,K+-ATPase.

N,N,6-Trimethyl-2-(4-methylphenyl)imidazo[1,2-a]-5,6,7,8-tetrahydropyridin-8-one-3-acetamide can be converted by reduction of the oxo group and subsequent elimination and aromatization to N,N,6-trimethyl-2-(4-methylphenyl)imidazo[1,2-a]pyridine-3-acetamide. The compound is commercially available as a non-benzodiazepine benzodiazepine agonist under the name Zolpidem (Ambien®).

1-(2-Chloroimidazo[1,2-a]-5,6,7,8-tetrahydropyridin-8-on-3-yl-sulfonyl)-3-(4,6-dimethoxypyrimidin-2-yl)urea can be converted by reduction of the oxo group and subsequent elimination and aromatization to Imazosulfuron® (1-(2-chloroimidazo[1,2-a]pyridin-3-ylsulfonyl)-3-(4,6-dimethoxypyrimidin-2-yl)urea).

1-(2-Ethylsulfonylimidazo[1,2-a]-5,6,7,8-tetrahydropyridin -8-on-3-ylsulfonyl)-3-(4,6-dimethoxypyrimidin-2-yl) urea can be converted by reduction of the oxo group and subsequent elimination and aromatization to Sulfosulfuron® (1-(2-ethylsulfonylimidazo[1,2-a]pyridin-3-ylsulfonyl)-3-(4,6-demethoxypyrimidin-2-yl)urea.

3-Amino-2-methylimidazo[1,2-a]-5,6,7,8-tetrahydropyridin-8-one can be converted by reaction, for example, with phenylmethyl bromide and subsequent aromatization by oxidation to 3-amino-2-methyl-8-(phenylmethoxy)imidazo [1,2-a]pyridine. A reaction with 2-phenylethylmagnesium bromide leads, after subsequent elimination of the hydroxyl group and aromatization, to 3-amino-2-methyl-8-(2-phenylethyl)imidazo[1,2-a]pyridine.

3-Formylimidazo[1,2-a]-5,6,7,8-tetrahydropyridin-8-one can be converted using methylmagnesium bromide and subsequent aromatization with elimination of the hydroxyl group to 3-formyl-8-methylimidazo[1,2-a]pyridine. This compound is suitable as an intermediate for the preparation of C-nucleoside analogs (as described in Pan SF et al. (1998) Tetrahedron Letters 39:8191–8194).

3-Formyl-7-methylimidazo[1,2-a]-5,6,7,8-tetrahyropyridin-8-one can be converted after reduction of the keto group, subsequent aromatization with elimination of the hydroxyl group to 3-formyl-7-methylimidazo[1,2-a]pyridine. This compound is suitable as an intermediate for the preparation of C-nucleoside analogs (such as described in Pan SF et al. (1998) Tetrahedron Letters 39:8191–8194).

Likewise particularly preferred is the preparation of the compounds mentioned in EP 0 930 062, preferably the compounds described below, for use in hair cosmetics starting from the imidazo[1,2-a]-5,6,7,8-tetrahyropyridin-8-ones according to the invention:

1. 8-Hydroxy-2,3-dimethylimidazo[1,2-a]pyridine. Preparation from 2,3-dimethylimidazo[1,2-a]-5,6,7,8-tetra -hyropyridin-8-one by means of oxidative aromatization.
2. 8-Amino-2,3-dimethylimidazo[1,2-a]pyridine. Preparation from 2,3-dimethylimidazo[1,2-a]-5,6,7,8-tetrahyropyridin-8-one by means of reaction with ammonia and oxidative aromatization.
3. 8-Hydroxy-3-hydroxymethyl-2-methylimidazo[1,2-a]pyridine. Preparation from 3-hydroxymethyl-2-methylimidazo[1,2-a]-5,6,7,8-tetrahydropyridin-8-one by means of oxidative aromatization.
4. 2-Methyl-3-hydroxymethyl-8-amino-imidazo[1,2-a]pyridine. Preparation from 3-hydroxymethyl-2-methylimidazo[1,2-a]-5,6,7,8-tetrahydropyridin-8-one-by means of reaction with ammonia and oxidative aromatization.
5. 8-Hydroxy-2,3-diethoxycarbonylimidazo[1,2-a]pyridine. Preparation from 2,3-diethoxycarbonylimidazo[1,2-a]-5, 6,7,8-tetrahydropyridin-8-one by means of oxidative aromatization.
6. 8-Amino-2,3-diethoxycarbonylimidazo[1,2-a]pyridine. Preparation from 2,3-diethoxycarbonylimidazo[1,2-a]-5, 6,7,8-tetrahydropyridin-8-one by means of reaction with ammonia and oxidative aromatization.
7. 8-Hydroxy-7-dimethylamino-2-methylimidazo[1,2-a]pyridine. Preparation from 7-dimethylamino-2-methylimidazo[1,2-a]-5,6,7,8-tetrahydropyridin-8-one by means of oxidative aromatization.
8. 8-Amino-7-dimethylamino-2-methylimidazo[1,2-a]pyridine. Preparation from 7-dimethylamino-2-methylimidazo[1,2-a]-5,6,7,8-tetrahydropyridin-8-one by means of reaction with ammonia and oxidative aromatization.
9. 8-Hydroxy-2,3-diethoxycarbonyl-7-methylimidazo[1,2-a]pyridine. Preparation from 2,3-diethoxycarbonyl-7-methylimidazo[1,2-a]-5,6,7,8-tetrahydropyridin-8-one by means of oxidative aromatization.
10. 8-Amino-2,3-diethoxycarbonyl-7-methylimidazo[1,2-a] pyridine. Preparation from 2,3-diethoxycarbonyl-7-methylimidazo[1,2-a]-5,6,7,8-tetrahydropyridin-8-one by means of reaction with ammonia and oxidative aromatization.
11. 2,7-Dimethyl-8-hydroxyimidazo[1,2-a]pyridine. Preparation from 2,7-dimethylimidazo[1,2-a]-5,6,7,8-tetrahydropyridin-8-one by means of oxidative aromatization.
12. 2,7-Dimethyl-8-aminoimidazo[1,2-a]pyridine. Preparation from 2,7-dimethylimidazo[1,2-a]-5,6,7,8-tetrahydropyridin-8-one by means of reaction with ammonia and oxidative aromatization.
13. 8-Hydroxy-2,3-bis(N,N-diethylamino)carbonylimidazo [1,2-a]pyri dine. Preparation from 2,3-(N,N-diethylamino)carbonyl -imidazo[1,2-a]-5,6,7,8-tetrahydropyridin-8-one by means of oxidative aromatization.
14. 8-Amino-2,3-bis(N,N-diethylamino)carbonylimidazo[1, 2-a]pyridine. Preparation from 2,3-(N,N-diethylamino) carbonyl -imidazo[1,2-a]-5,6,7,8-tetrahydropyridin-8-one by means of reaction with ammonia and oxidative aromatization.
15. (8-Hydroxy-2-methylimidazo[1,2-a]pyridin-3-yl)acetonitrile. Preparation from 2-methyl-3-acetonitrileimidazo [1,2-a]-5,6,7,8-tetrahydropyridin-8-one by means of oxidative aromatization.
16. (8-Amino-2-methylimidazo[1,2-a]pyridin-3-yl)acetonitrile. Preparation from 2-methyl-3-acetonitrileimidazo[1, 2-a]-5,6,7,8-tetrahydropyridin-8-one by means of reaction with ammonia and oxidative aromatization.

Preferred compounds of the general formula V are mentioned in WO 98/42707. In particular, the compounds according to the invention 3-formyl-2-methylimidazo[1,2-a]-5,6,7,8-tetrahydropyridin-8-one, 3-hydroxymethyl-2-methylimidazo[1,2-a]-5,6,7,8-tetrahydropyridin-8-one or 2,3-dimethylimidazo[1,2-a]-5,6,7,8-tetrahydropyridin-8-one can be converted according to reaction scheme C to one of the following compounds:

2,3-Dimethylimidazo[1,2-a)-5,6,7,8-tetrahydropyridin-8-one to:
a) 2,3-Dimethyl-9-phenyl-7,8,9, 10-tetrahydroimidazo[1,2-h][1,7]naphthyridin-7-one.
b) 9-(2-Chlorophenyl)-2,3-dimethyl-7,8,9,10-tetrahydroimidazo[1,2-h][1,7]naphthyridin-7-one.
c) 9-(2,6-Dichlorophenyl)-2,3-dimethyl-7,8,9,10-tetrahydroimidazo[1,2-h][1,7]naphthyridin-7-one.
d) 9-(2-Trifluoromethylphenyl)-2,3-dimethyl-7,8,9,10-tetrahydroimidazo[1,2-h][1,7]naphthyridin-7-one.
e) 7-Hydroxy-2,3-dimethyl-9-phenyl-7,8,9,10-tetrahydroimidazo[1,2-h][1,7]naphthyridine.
f) 9-(2-Chlorophenyl)-7-hydroxy-2,3-dimethyl-7,8,9,10-tetrahydroimidazo[1,2-h][1,7]naphthyridine.
g) 9-(2,6-Dichlorophenyl)-7-hydroxy-2,3-dimethyl-7,8,9, 10-tetrahydroimidazo[1,2-h]][1,7]naphthyridine.
h) 9-(2-Trifluoromethylphenyl)-7-hydroxy-2,3-dimethyl-7, 8,9,10-tetrahydroimidazo[1,2-h][1,7]naphthyridine.
i) 8-Hydroxy-2,3-dimethyl-9-phenyl-7,8,9,10-tetrahydroimidazo -[1,2-h][1,7]naphthyridin-7-one.
j) 7,8-Dihydroxy-2,3-dimethyl-9-phenyl-7,8,9,10-tetrahydroimidazo[1,2-h][1,7]naphthyridine.

k) 7,8-Isopropylidendioxy-2,3-dimethyl-9-phenyl-7,8,9,10-tetrahydroimidazo[1,2-h][1,7]naphthyridine.

3-Formyl-2-methylimidazo[1,2-a]-5,6,7,8-tetrahydropyridin-8-one to:
a) 3-Formyl-8-hydroxy-2-methyl-7-oxo-9-phenyl-7,8,9,10-tetrahydroimidazo[1,2-h][1,7]naphthyridine.

Preferably, the formyl group here is employed protected as an acetal.

3-Hydroxymethyl-2-methylimidazo[1,2-a]-5,6,7,8-tetrahydropyridin -8-one to:
a) 3-Hydroxymethyl-7,8-dihydroxy-2-methyl-9-phenyl-7,8,9,10-tetrahydroimidazo[1,2-h][1,7]naphthyridine.

Preferably, the hydroxymethyl group is employed protected in the form of an ether or-ester.

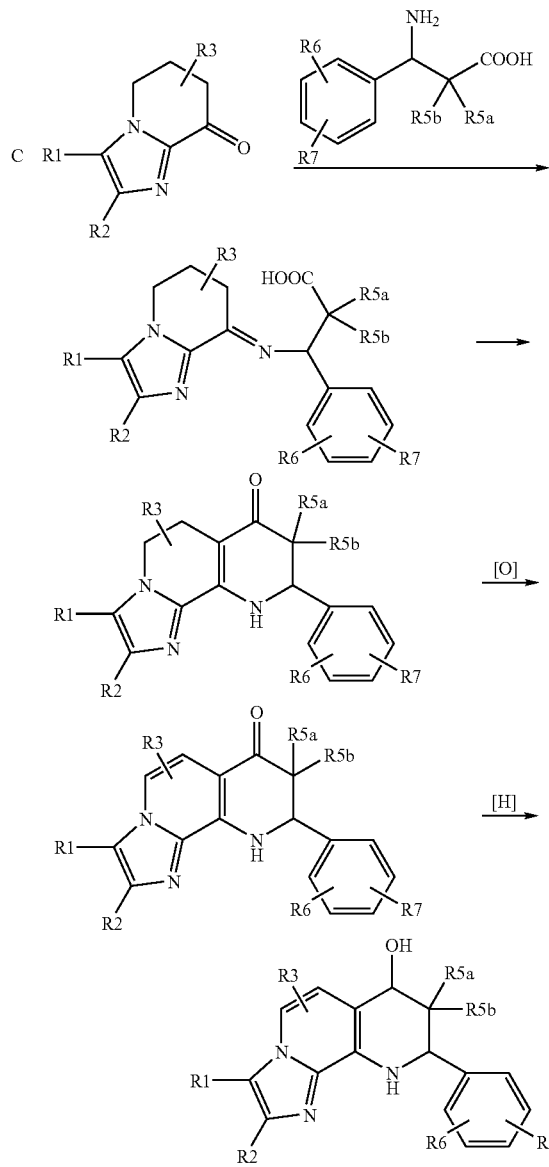

-continued

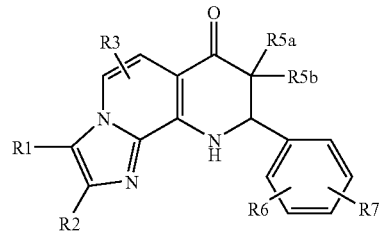

EXAMPLE 1

Preparation of 2,3-dimethylimidazo[1,2a]-5,6,7,8-tetrahydropyridin-8-one 25 mol (2130 g) of distilled γ-butyolactone dist. (corresponding to 1.89 l) were introduced into a 4 l four-necked flask and 5 mol (500 g) of 4,5-dimethylimidazole (96% strength) were introduced. The mixture was heated up under a protective gas atmosphere (pass over a stream of nitrogen of about 15 l/h) at 190° C. to 200° C. and stirred for 10 hours, the temperature continuously being increased to 215° C. In the course of this, the resulting water of reaction and excess butyrolactone were distilled off (amount of distillate: about 1000 g).

After 10 hours, a sample of the reaction was investigated with respect to the desired product by gas chromatography. In the case of a positive result, the reaction mixture was cooled to 25° C. in the course of 8 hours. The reaction mixture was filtered through an 18 cm porcelain suction filter. The filter cake was washed with 100 g of γ-butyrolactone via the reaction flask and sucked well dry. The filter cake was then stirred in 450 g of acetone, filtered off with suction again and washed with 50 g of acetone. After sucking dry, the filter cake is dried at 70° C. in vacuo. This yield was 30% based on the imidazole.

EXAMPLE 2

Preparation of 2-methylimidazo[1,2a]-5,6,7,8-tetrahydropyridin-8-one and 3-methylimidazo[1,2a]-5,6,7,8-tetrahydropyridin-8-one 0.75 mol (64.5 g) of distilled γ-butyrolactone was introduced into a 250 ml three-necked flask and 0.15 mol (12.3 g) of 4-methylimidazole (97% strength) were introduced. The reaction vessel was inertized with nitrogen and a continuous stream of nitrogen of about 10 l/h was passed over during the reaction. The reaction mixture was heated to 190° C. with stirring in the course of 2 hours and kept at this temperature for a further 8 hours. During the reaction time, about 5 g of distillate consisting of water which forms in the reaction and γ-butyrolactone were collected. The reaction mixture was cooled and the discharge was concentrated on a rotary evaporator until γ-butyrolactone no longer passed over. The isolation of the two isomeric reaction products was carried out by bulb tube distillation of the bottom at 180° C. and 0.4 mbar. 4.5 g (0.03 mol; 20% of the theoretical maximum yield) of 2-methylimidazo[1,2a]-5,6,7,8-tetrahydro -pyridin-8-one and 3-methylimidazo[1,2a]-5,6,7,8-tetrahydro -pyridin-8-one in the ratio of about 1:1 (according to NMR) were obtained as a pale oil.

EXAMPLE 3

Preparation of 2,3-diphenyl-5,6,7,8-tetrahydro-imidazo[1l,2a]pyridin-8-one

A 100 ml four-necked flask was charged with 0.3 mol (26 g) of distilled-butyrolactone (corresponding to 23 ml) and 0.1 mol (22 g) of 4,5-diphenylimidazole was added. Under a protective gas atmosphere, the mixture was heated to 180° C. and stirred for 20 hours. The resulting water of reaction was distilled off in the process.

After 20 hours, a sample of the reaction mixture was investigated with respect to the desired product by gas chromatography. In the case of the positive result, the reaction mixture was cooled to 80° C. in the course of 5 hours. The batch was filtered through a 5.5 cm glass suction filter at 80° C. The filter cake was washed with 10 g of butyrolactone via the reaction flask and sucked well dry. The filter cake was then washed with 15 g of acetone. After sucking dry, the filter cake was dried at 70° C. in vacuo. The yield with this run was 19% based on the imidazole.

2,3-Diphenyl-5,6,7,8-tetrahydroimidazo[1,2a]pyridin-8-one was obtained and identified by NMR spectroscopy.

We claim:

1. A process for the preparation of imidazo-[1,2a]-5,6,7,8-tetra-hydropyridin-8-ones, of the formula

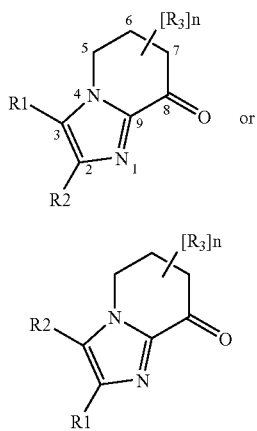

which comprises
a) reacting a γ-butyrolactone of the formula III

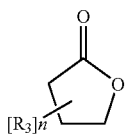

with an imidazole of the formula IIa or IIb

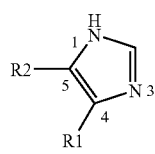

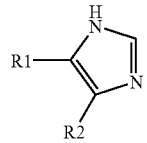

wherein at least one of $R^1$ or $R^2$ is different from hydrogen, and
b) isolating the imidazo[1,2a]-5,6,7,8-tetrahydropyridin-8-one, where R1, R2 or every R3 is simply independently selected from the group consisting of hydrogen, unsubstituted, branched or unbranched or cyclic alkyl, substituted or unsubstituted aryl, where the number of substituents R3 can assume a value n from 1 to 3.

2. The process as claimed in claim 1, wherein the reaction mixture is heated to temperatures from 150° C. to 250° C.

3. A process as claimed in claim 1, wherein the γ-butyrolactone is employed in excess.

4. A process as claimed in claim 1, wherein the γ-butyrolactone is used as a solvent and during or after the reaction the water of reaction and some or the total amount of the excess γ-butyrolactone is removed.

5. A process as claimed in claim 1, wherein R1 and R2 are not hydrogen.

6. A process as claimed in claim 1, wherein R1 and R2 are identical.

7. A process as claimed in claim 1, wherein R1 and R2 are methyl and R3 is hydrogen.

8. A process for the production of an imidazo[1,2a]pyridine, said process comprising preparing an imidazo[1,2a]-5,6,7,8-tetrahydropyridin-8-one of the formula Ia or Ib by the process of claim 1, and further comprising reacting the imidazol of formula Ia or Ib with an aryl- or alkylamine and subsequent oxidative aromatization, or with ammonia, subsequent oxidative aromatization and alkylation or arylation or oxidative aromatization and subsequent alkylation or arylation.

9. The process according to claim 8, wherein the imidazo[1,2a]pyridine is described by the formula IV

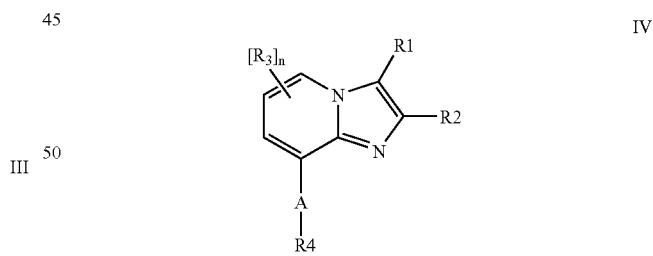

and
a) where the number of substituents R3 can assume a value n from 1 to 3 and
b) A is O or NH, and
c) R4 is selected from the group consisting of substituted or unsubstituted, branched or unbranched $C_1$–$C_6$-alkyl, $C_2$–$C_6$-alkenyl, $C_2$–$C_6$-alkynyl, $C_3$–$C_7$cycloalkyl, $C_3$–$C_6$-alkadienyl, halo-$C_1$–$C_6$-alkyl, $C_1$–$C_6$-alkoxy, $C_2$–$C_6$-alkenyloxy, $C_2$–$C_6$-alkynyloxy, $C_1$–$C_6$-alkyloxy-$C_1$–$C_6$-alkyl, $C_1$–$C_6$-alkyloxy-$C_2$–$C_6$-alkenyl, $C_1$–$C_6$-alkyloxy-$C_2$–$C_6$alkynyl, cyano-$C_1$–$C_6$-alkyl, isocyano-$C_1$–$C_6$-alkyl, amino-$C_1$–$C_6$-alkyl, amino- $C_2$–$C_6$-alkyl, carboxyl, $C_1$–$C_6$-alkylcarboxyl, substituted or unsubstituted aryl, arylalkyl, heteroaryl and heteroarylalkyl.

10. A process for the production of an imidazo[1,2a] pyridine, said process comprising preparing an imidazo[1,2a]-5,6,7,8-tetrahydropyridin-8-one of the formula Ia or Ib by the process of claim 1, further comprising reacting an imazdol of formula Ia or Ib with a 2-amino-3-phenylpropionic acid and subsequent oxidation and optionally subsequent hydrogenation to obtain compounds of formula V

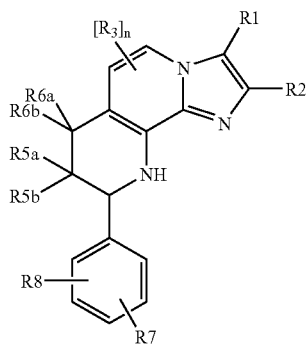

V where a) the number of substituents R3 can assume a value n from 1 to 2 and b) R5a and R5b are selected from the group consisting of hydrogen, hydroxyl, $C_1$–$C_6$-alkoxy, $C_1$–$C_6$-alkoxy-$C_1$–$C_6$-alkoxy, $C_1$–$C_6$-alkylcarbonyloxy, where R5a and R5b can also together be oxygen (oxo group), and c) R6a and R6b are selected from the group consisting of hydrogen, hydroxyl, $C_1$–$C_6$-alkoxy, $C_1$–$C_6$-alkoxy-$C_1$–$C_6$-alkoxy, $C_1$–$C_6$-alkylcarbonyloxy, where at least one of the radicals R6a or R6b is hydrogen and where R6a and R6b can also together be oxygen (oxo group), and d) R7 is selected from the group consisting of hydrogen, halogen, $C_1$–$C_6$-alkyl, $C_1$–$C_6$-alkoxy, $C_1$–$C_6$-alkoxycarbonylamino, $C_1$–$C_6$-alkoxy-$C_1$–$C_6$-alkoxycarbonylamino or trifluoromethyl, and e) R8 is selected from the group consisting of hydrogen, halogen, $C_1$–$C_6$-alkyl, $C_1$–$C_6$-alkoxy.

* * * * *

UNITED STATES PATENT AND TRADEMARK OFFICE
CERTIFICATE OF CORRECTION

PATENT NO. : 7,196,196 B2 Page 1 of 1
APPLICATION NO. : 10/488751
DATED : March 27, 2007
INVENTOR(S) : Weigl et al.

It is certified that error appears in the above-identified patent and that said Letters Patent is hereby corrected as shown below:

In claim 9, column 20, indicated line 66: "$C_1$-$C_6$-alkyloxy-$C_2$-$C_6$alkynyl" should read --$C_1$-$C_6$-alkyloxy-$C_2$-$C_6$-alkynyl--

In claim 9, column 20, indicated line 67 – column 21, indicated line 1: "amino-$C_2$-$C_6$-alkyl" should read --amino-$C_2$-$C_6$-alkynyl--

Signed and Sealed this

Thirty-first Day of July, 2007

JON W. DUDAS
*Director of the United States Patent and Trademark Office*